United States Patent [19]

Klearman et al.

[11] Patent Number: 5,553,793
[45] Date of Patent: Sep. 10, 1996

[54] COMBINATION PILL CRUSHING AND DISPENSING CUP

[75] Inventors: Jeffrey D. Klearman; Robert Bronson, both of St. Louis, Mo.

[73] Assignee: Lake Medical Products, Inc., St. Louis, Mo.

[21] Appl. No.: 288,599

[22] Filed: Aug. 10, 1994

Related U.S. Application Data

[63] Continuation-in-part of Ser. No. 168,019, Dec. 15, 1993, Pat. No. 5,376,072.

[51] Int. Cl.$^6$ .................................................. B02C 19/08
[52] U.S. Cl. ........................ 241/30; 241/169.2; 241/199; 241/DIG. 27
[58] Field of Search ........................ 241/21, 169.2, 241/199, DIG. 27, 30

[56] References Cited

U.S. PATENT DOCUMENTS

| | | | |
|---|---|---|---|
| 1,165,686 | 12/1915 | McElroy . | |
| 2,602,596 | 7/1952 | Jones et al. | 241/DIG. 27 X |
| 2,892,595 | 6/1959 | Tupper | 241/199 |
| 3,915,393 | 10/1975 | Elkins | 241/168 |
| 4,057,052 | 11/1977 | Kaufman et al. . | |
| 4,209,136 | 6/1980 | Linden et al. | 241/169.2 |
| 4,366,930 | 1/1983 | Trombetti, Jr. | 241/169 |
| 4,568,331 | 2/1986 | Fischer et al. | 604/56 |
| 4,715,854 | 12/1987 | Vaillancourt | 604/191 |
| 4,765,549 | 8/1988 | Sherman | 241/169 |
| 4,967,971 | 11/1990 | Smith | 241/169 |
| 5,067,666 | 11/1991 | Sussman | 241/36 |
| 5,118,021 | 1/1992 | Fiocchi | 225/103 |
| 5,148,995 | 9/1992 | Hurst | 241/30 |
| 5,322,227 | 6/1994 | Fiocchi | 241/100 |

OTHER PUBLICATIONS

American Medical Industries brochure entitled "Making Your Medications & Vitamins EZ to Swallow", including enclosure entitled Remembering Your Medication Schedule is EZ (no date given).
American Medical Industries sales flier entitled "Welcome to American Medical Industries" Family of EZ-Health™ Products, 1993.
American Medical Industries Facsimile transmission to Lake Medical Products regarding EZ-SWALLOW Pill Crushers & Pill Splitters, Sep. 1, 1993.
Gerber Products Company, BABY MEDI-SPOON, 1991.

*Primary Examiner*—John Husar
*Attorney, Agent, or Firm*—Howell & Haferkamp, L.C.

[57] ABSTRACT

Two pill crushing/dispensing cups are provided, each having an interior and an exterior abraded surface on the cup bottom. A pill is placed within a first of the cups and a second cup is nested within the first such that the pill is positioned between the first cup interior knurled surface and the second cup exterior knurled surface. The pill is crushed as the second cup is rotated and advanced within the first cup, a fluid is added to the first cup forming a fluid/pill crushing suspension therein, and the suspension is orally administered directly from the first cup. Both cups may be identical in design.

17 Claims, 1 Drawing Sheet

COMBINATION PILL CRUSHING AND DISPENSING CUP

CROSS-REFERENCE TO RELATED APPLICATION

This application is a continuation-in-part of Ser. No. 08/168,019, filed Dec. 15, 1993, now U.S. Pat. No. 5,376,072.

BACKGROUND AND SUMMARY OF THE INVENTION

Administering medication and vitamins, in tablet or capsule form to infants, the elderly, and otherwise feeble hospital patients can be problematic. Not only do these patients have difficulty swallowing the pills, when feeble hospital patients die it is not uncommon for an autopsy to reveal multiple intact pills within the deceased body because the liver failed to produce sufficient enzymes to break through the pill shell. This, of course, prohibits the medication from being dispersed timely into the bloodstream and may contribute to the patient's death. As a result, medication such as aspirin, antibiotics, and other drugs are frequently available in liquid form for easy administration to hospital patients experiencing difficulty with pills and capsules.

For those instances where the medication is only available in pill or capsule form, the pills are frequently crushed in a first container (i.e. with a pestle and mortar), and the pill crushings are then transferred to a second container or dispensing utensil where they can be mixed with a fluid for oral administration to the patient. As detailed in the parent, hereto, there are several drawbacks with the above pestle and mortar technique such as the risk of low and unpredictable dosage compliance, cross-contamination, and the necessity to purchase and maintain inventory of multiple utensils and containers for the crushing, mixing, and dispensing tasks. As disclosed and claimed in the parent, the disclosure of which is incorporated herein by reference, a similar problem of administering medication in pill or capsule form exists for comatose and many infirm adult patients physically unable to swallow medication in pill or capsule form. The solution thereto was provided by the pill-crushing syringe disclosed and claimed in the parent. The invention disclosed and claimed therein is a good and valuable invention which itself may be used to crush pills for suspension in a fluid for administration principally through an intravenous tube or the like but which may also be administered orally. Although the pill crushing syringe itself represents an elegantly simple design which is amendable to low cost, high volume manufacture, the inventor herein has continued his search to further extend his pill crushing concept to even simpler designs at even lower cost.

In order to solve these and other problems in the prior art, and as an extension of the general concept disclosed and claimed in the parent hereto, the inventors herein have succeeded in designing and developing a single use pill dispensing cup with a cup bottom having an knurled surface on its interior and exterior surface. The cup is designed to nest and, when used as a nesting pair, a pill may be placed between an upper and lower cup and crushed between the two knurled surfaces on the interior and exterior of the cup bottoms. Although prior art single use medicine dispensing cups are typically thin walled and flexible, the present invention contemplates a more substantial construction for the cup so as to withstand the force required to crush the pill as the cups are pushed together against the pill and twisted. Additionally, if desired, the cup may have a wider lip to provide a finger grip for the hands as the cups are twisted together.

The knurled surfaces on the interior and exterior surface of each cup bottom are formed from a plurality of pyramidal shaped protrusions with the protrusions having a flatter angle on the exterior surface than on the interior surface. This flatter angle on the exterior surface makes it less likely that pill crushings will be trapped between the protrusions and instead will remain within the bottom cup. After the pill is crushed, fluid is added to the bottom cup to create the suspension which may then be administered. If there are any pill crushings climbing to the exterior surface of the top cup, it may be conveniently "dunked" in the fluid contained in the lower cup and agitated to remove any remaining pill crushings therefrom. This helps to insure high dosage compliance.

After a nested pair are used to crush and administer a pill, they may be conveniently discarded because of their low cost and this eliminates any risk of cross contamination. As a single cup design is used, it may be readily manufactured at high volume using plastics such as polypropylene or polyethylene and thereby produced at a very low cost. Furthermore, the pill crushing feature of the invention is an added bonus and need not be used should the cups be desired simply for dispensing medication as with the prior art cups presently used.

While the principal advantages and features of the present invention have been briefly described above, a more thorough understanding and appreciation for the invention's advantages and features may be attained by referring to the drawings and descriptions of the preferred embodiment which follow.

DESCRIPTION OF THE PREFERRED EMBODIMENT

Figure 1:
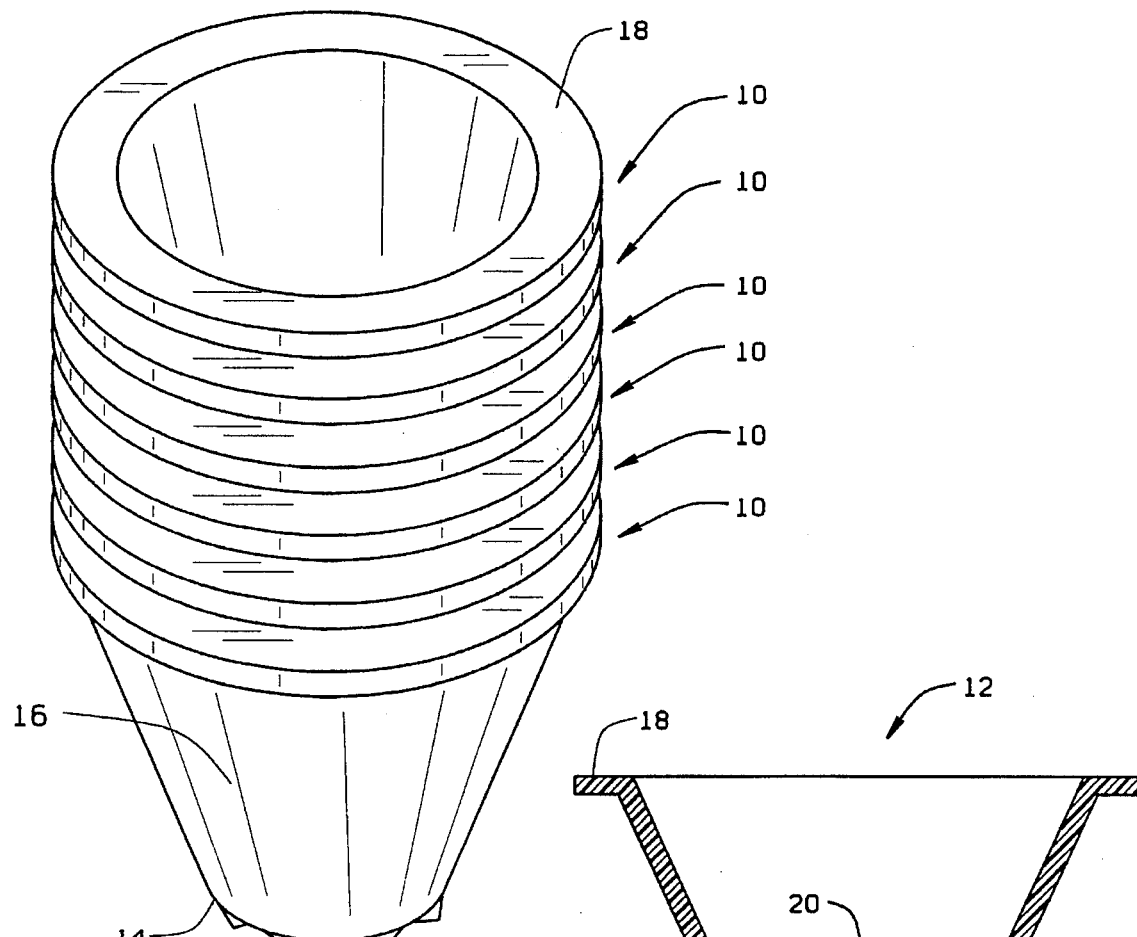
FIG. 1 is an isometric view of a plurality of nested pill crushing/dispensing cups of the present invention.
Figure 2:
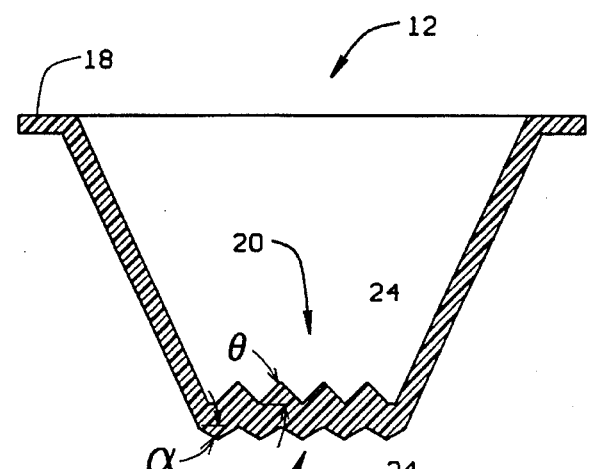
FIG. 2 is a cross-sectional view of one pill crushing/dispensing cup illustrating the interior and exterior knurled surfaces.

A plurality of pill crushing/dispensing cups 10 constructed according to the principles of this invention are illustrated in FIG. 1 stacked atop one another in nested fashion. Each cup includes an open top 12, a closed bottom 14, and a frustoconic wall 16 having a rim 18. The rim 18 is preferably one-quarter inch wide, measured radially, which is sufficiently wide to provide a grip for the fingers to facilitate pushing one of the cups 10 downward into another cup 10. The cups 10 are preferably constructed of styrenic plastic which is light weight but significantly stronger than the cups typical in the prior art. As illustrated in FIG. 2, the bottom 14 includes an interior knurled surface 20 and an exterior knurled surface 22. Alternately, the abraded surfaces may be located at other locations on the cup, such as on the frustoconic wall 16. If located on the side wall 16, the surfaces could conveniently be aligned and a pill crushed therebetween as two cups are nested and twisted against each other. Although preferable, it is not necessary that the pill be crushed as two cups are nested but only that a pill can be crushed by the knurled surfaces.

Preferably, the knurled surfaces 20 and 22 include a plurality of pyramidal shaped protrusions 24 having faces extending from the bottom 14 at an angle θ and α with respect to a horizontal line drawn parallel to the bottom, respectively. In the preferred embodiment the angle θ (interior) is larger than the angle α so that crushed pill particles are less likely to lodge between the protrusions 24 of the exterior knurled surface 22. Preferably θ equals 45° and α equals 30°. Further, the exterior knurled surface 22 includes a protrusion pattern wherein the protrusion tips are level relative to each other (see FIG. 2) and are sufficiently spaced to sturdily support the cup 10 on a tray, cart, table, or other horizontal surface.

Figure 3:
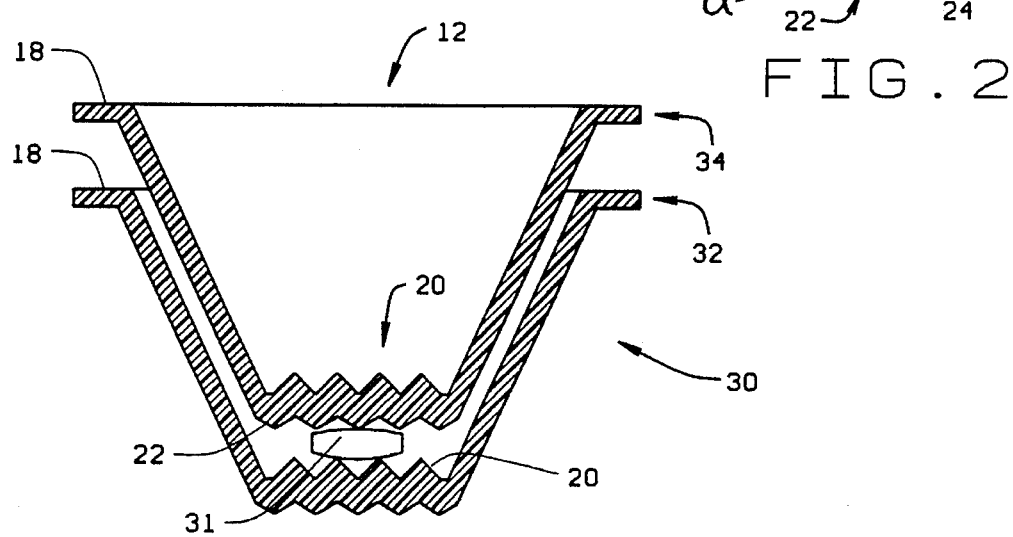
FIG. 3 is a cross-sectional view of a nested pair of the pill crushing/dispensing cups of the present invention.

This frustoconic design facilitates nesting the cups 10 one atop another thereby allowing large numbers of cups to be stored in a relative small area. FIG. 3 illustrates a nested pair 30 of the cups 10 with a pill 31 positioned therein. The nested pair 30 includes a base cup 32 and a top cup 34 wherein the exterior knurled surface 22 of the top cup 34 is positioned above the interior knurled surface 20 of the base cup 32 when the base cup is positioned upright. Because the cups are designed and manufactured substantially identical to one another, any two cups may be selected from a large supply of the cups 10 to form the nested pair 30.

In operation, a nurse or other health-care professional divides the appropriate quantity of medication to be administered to a given patient and places the pills/capsules in a cup 10 much like the procedure presently used in the prior art to distribute medicated pills and capsules. If a given patient is able to swallow the pills without difficulty, the cup 10 is well suited to perform the function of the flimsy conventional cups utilized by hospitals in the prior art (i.e. merely containing the medication dosage during transport). The level and spaced protrusion pattern on the exterior knurled surface 22 of the cup bottom 14 provides a sturdy foundation for the cup to rest on the medication trays or carts commonly used in the prior art to transport medication to patients' rooms.

However, if a patient requires, or simply desires, the medication to be suspended in a liquid, this elegant cup design easily facilitates such a request. Rather than selecting a single cup 10, the nurse selects a pair of cups. The nested pair 30 is pulled apart and a pill 31 (or a capsule) is placed within the base cup 32. The top cup 34 is repositioned within the base cup 32 such that the pill is lodged snugly between the interior abraded knurled surface 20 of the base cup 32 and the exterior knurled surface 22 of the top cup 34. The cups 32 and 34 are then preferably twisted in opposite directions while being advanced closer together thereby crushing and grinding the pill therebetween. The rim 18 of the top cup 34 provides a convenient finger grip for the hand while pushing and twisting the cups 32 and 34 together. While in an upright position, the top cup 34 is removed from the base cup 32 and a liquid is added to the base cup thereby forming a suspension of the pill crushings. If desired, the bottom of the top cup 34 may be washed off by dipping it into the liquid. This will ensure that virtually all of the pill pets administered to the patient. The suspension is then orally administered directly from the base cup 32.

Because the angle α is preferably only 30°, it is unlikely that any pill crushings will lodge within the exterior knurled surface 22 thereby promoting high-dosage compliance. Moreover, the top cup 34 may be gently tapped against the interior wall of the base cup 32 as it is removed therefrom to further assure that the pill crushings and pill residue are removed from the exterior of top cup 34. While the 45° angle θ may trap a few pill crushings between the interior abraded surface protrusions of the base cup 32, the liquid added to the base cup 32 helps to dislodge any of these pill crushings or residue from the interior knurled surface 20. This, again, contributes to high-dosage compliance. Moreover, this simple design is well adapted for economical mass production thereby making it cost effective to dispose of the top cup 34 and the base cup 32 after only a single use thereby minimizing any risk of cross-contamination.

Although illustrated embodiments of the present invention are described herein with reference to the accompanying drawings, it is understood that the invention is not limited to those precise embodiments and that various other changes and modifications may be effected therein by one skilled in the art without departing from the scope or spirit of the invention. The scope of the invention is defined solely by the claims, and their equivalents, appended hereto.

What is claimed is:

1. A pill crushing device including a cup having an exterior knurled surface and an interior knurled surface, the knurled surfaces being configured to enable the cup be used as a knurled pestle or a knurled mortar.

2. The device of claim 1 wherein said cup constitutes a first cup, said device further including a second cup having an exterior knurled surface and an interior knurled surface, said first and second cups being nestable within each other.

3. The device of claim 2 wherein the exterior knurled surface of said first cup is positioned to engage the interior knurled surface of said second cup as said cups are nested so that a pill placed between said cups and adjacent said knurled surfaces may be crushed as said cups are nested.

4. The device of claim 3 wherein said first cup is rotatable within said second cup to thereby facilitate grinding a pill placed therebetween and adjacent said knurled surfaces.

5. The device of claim 4 wherein each of said cups has an open top and a closed bottom, said knurled surfaces being located on the interior and exterior of said cup bottom.

6. The device of claim 5 wherein said knurled surfaces comprise a plurality of protrusions, said exterior knurled surface protrusions being formed at a flatter angle than said interior knurled surface protrusions such that pill crushings are less likely to adhere to the exterior knurled surface.

7. The device of claim 6 wherein said exterior knurled surface angle is approximately 30°.

8. A combination pill crushing and dispensing device comprising an interchangeable nestable pair of cups, including a top cup, a base cup, and at least one knurled surface on one of said cups, each of said cups having sidewalls and being sufficiently rigid so that a crushing force is generated at said knurled surface and against a pill placed between the cups as said sidewalls are grasped and said cups are manually advanced into a nesting configuration.

9. The device of claim 8 wherein the top cup includes at least one exterior knurled surface, and wherein the base cup includes at least one interior knurled surface positioned to engage the top cup knurled surface as the two cups are nested.

10. The device of claim 9 wherein the top cup and the base cup each include a closed bottom on which the respective knurled surfaces are located.

11. The device of claim 10 wherein the sidewall of said base cup is formed at an angle which permits the top cup to rotate therein to thereby grind a pill placed therebetween and adjacent said knurled surfaces.

12. The device of claim 11 wherein said base cup further includes an exterior knurled surface on said closed bottom and said top cup further includes an interior knurled surface on said closed bottom.

13. The device of claim 12 wherein the top cup and the base cup are substantially identical.

14. The device of claim 13 wherein said knurled surfaces comprise a plurality of protrusions, said exterior knurled surface protrusions being formed at a flatter angle than said interior knurled surface protrusions such that pill crushings are less likely to adhere to the exterior knurled surface.

15. The device of claim 14 wherein each cup has a rim to provide a finger grip therefor as said pill is crushed.

16. A method of crushing a pill and dispensing the pill crushings suspended in a fluid, wherein first and second cups are provided, at least one of the cups including a knurled surface, the method comprising the steps of:

placing a pill in the first cup;

nesting the second cup into the first cup so that the knurled surface twisting the cups with respect to each other as the second cup is advanced into the first cup to cause the knurled surface to grind and thereby crush the pill;

mixing the pill crushings with a fluid thereby suspending the pill crushings; and dispensing the suspension.

17. The method of claim 16 wherein the mixing step includes the step of adding the fluid to the first cup and said dispensing step includes the step of orally administering the suspension directly from the first cup.

* * * * *

UNITED STATES PATENT AND TRADEMARK OFFICE
CERTIFICATE OF CORRECTION

PATENT NO. : 5,553,793
DATED : September 10, 1996
INVENTOR(S) : Klearman, et al.

It is certified that error appears in the above-indentified patent and that said Letters Patent is hereby corrected as shown below:

In the Abstract of the Disclosure, first sentence, replace "abraded" with --knurled--.
In column 2, line 13, replace "climbing" with --clinging--.
In column 2, line 10, replace "abraded" with --knurled--.
In column 3, line 46, delete "abraded".
In column 3, line 58, replace "pets" with --gets--.
In column 3, line 67, replace "abraded" with --knurled--.
In column 4, line 20, after the word "cup", insert the --to--.
In column 6, line 2, after the word "surface", insert --engages the pill;--.

Signed and Sealed this

Thirty-first Day of December, 1996

BRUCE LEHMAN

Attest:

Attesting Officer

Commissioner of Patents and Trademarks